United States Patent [19]

Hommeltoft

[11] Patent Number: 5,625,114
[45] Date of Patent: Apr. 29, 1997

[54] PROCESS FOR THE RECOVERY OF SPENT ACID CATALYST

[75] Inventor: Sven I. Hommeltoft, Hillerød, Denmark

[73] Assignee: Haldor Topsøe A/S, Denmark

[21] Appl. No.: 450,389

[22] Filed: May 25, 1995

[30] Foreign Application Priority Data

Jun. 2, 1994 [DK] Denmark ................................. 0622/94

[51] Int. Cl.$^6$ .............................. C07C 2/58; B01J 20/34
[52] U.S. Cl. ........................... 585/731; 585/730; 502/31; 502/33
[58] Field of Search .................... 585/730, 731; 502/31, 33

[56] References Cited

U.S. PATENT DOCUMENTS 5,220,095  6/1993  Hommeltoft et al. ................. 585/720

Primary Examiner—Helane Myers
Assistant Examiner—In Suk Bullock
Attorney, Agent, or Firm—Ostrolenk, Faber, Gerb & Soffen, LLP

[57] ABSTRACT

A process for the recovery of a sulphonic acid catalyst from an aqueous extract of an alkylation effluent stream comprising the steps of evaporating the extract to obtain a hydrate of the sulphonic acid catalyst;

reacting the hydrate with an olefin containing hydrocarbon stream to its corresponding sulphonic acid ester; and introducing the acid ester to a process for the alkylation of a hydrocarbon feedstock with an olefinic alkylation agent at alkylation conditions, thereby decomposing the sulphonic acid ester to its acid form being catalytic active in the alkylation process.

6 Claims, No Drawings

PROCESS FOR THE RECOVERY OF SPENT ACID CATALYST

The present invention relates to certain improvements in the catalytic alkylation of aliphatic hydrocarbons in the presence of an acid catalyst, and, more particular, to the recovery of such catalyst from an oil by-product being formed during the processes.

Acid catalyzed alkylation of aliphatic hydrocarbons with olefinic hydrocarbons is a well-known process for the preparation of high octane gasoline products. Alkylation of aliphatic hydrocarbons is generally accomplished in the liquid phase by reacting paraffins and olefins in the presence of a strong acid catalyst.

Conventionally used acids in industrial alkylation processes are hydrogen fluoride and sulphuric acid.

Utilization of fluorinated sulphonic acids as efficient alkylation catalysts in the alkylation of aliphatic hydrocarbons with olefins, is disclosed in U.S. Pat. No. 5,220,095, which by reference is enclosed herein. By the disclosed process, a process stream, including a hydrocarbon substrate and an olefinic alkylating agent, is reacted in contact with a fluorinated sulphonic acid catalyst in a fixed bed alkylation reactor containing polar contact material. On the contact material is established a reaction zone with the fluorinated sulphonic acid catalyst adsorbed within a confined area of the contact material. In the reaction zone, the process stream is converted at alkylating conditions to a product stream of alkylated hydrocarbons by catalysis of the fluorinated sulphonic acid adsorbed on the contact material.

During the alkylation reaction, the acid catalyst and, consequently, the reaction zone moves as a well-defined band between the ends of the reactor due to interaction with the process stream flowing through and reacting in the zone.

When migrating on the contact material, the catalytic activity of the fluorinated sulphonic acid is substantially retained and the acid is still catalytically active, when the reaction zone reaches the reactor outlet.

Although it is possible to reuse the acid catalyst without recovery of the acid as it reaches the outlet end of the alkylation reactor by reversing the flow direction of the process stream introduced into the alkylation reactor, small amounts of the acid catalyst will continuously be trapped in an acid soluble oil by-product being formed by side reactions during the process. The oil adsorbs like the acid catalyst as a movable band on the support material adjacent to the reaction zone. It is, thus, possible to withdraw the oil from the reactor, whenever the oil band reaches one of the ends of the reactor.

Even if the oil contains only small amounts of spent acid catalyst, it is desirable to recover the catalyst in order to improve the economy of the alkylation process. Conventional methods, like distillation or extraction of the acid directly from the oil, are not applicable because of strong interaction between the acid catalyst and basic components in the oil.

Recovery of spent fluorinated sulphonic acid by extraction of an effluent stream from an alkylation reactor by washing with water is disclosed in the aforementioned U.S. patent. The obtained aqueous acid solution is by the disclosed process subjected to a sequence of concentration and distillation steps.

It has now been found that extraction of spent acid catalyst from an alkylation effluent stream is improved by a simple process route of converting the acid into its hydrate form and treating the hydrate with a suitable esterification agent to obtain an ester of the acid. The ester can then be extracted into a hydrocarbon stream and recycled to the alkylation process.

Accordingly, a broad embodiment of the invention is directed towards a process for the recovery of a sulphonic acid catalyst from an aqueous extract of an an alkylation effluent stream comprising the steps of evaporating the extract to obtain a hydrate of the sulphonic acid catalyst;

reacting the hydrate with an olefin containing hydrocarbon stream to its corresponding sulphonic acid ester; and introducing the acid ester into a process for the alkylation of a hydrocarbon feedstock with an olefinic alkylation agent at alkylation conditions, thereby decomposing the sulphonic acid ester to its acid form being catalytically active in the alkylation process.

The method according to the invention is useful in the recovery of halogenated alkyl sulphonic acid alkylation catalysts, in particular, recovery of trifluoromethanesulphonic acid.

Extraction of the acid soluble oil during recovery of spent acid catalyst from industrial alkylation units may be carried out in stirred backmix reactors.

As an alternative, extraction may also be accomplished in a continuously operated extraction column with the aqueous extract in countercurrent with the olefinic hydrocarbon stream.

In still a preferred embodiment, the acid hydrate is treated with an alkylation process stream containing butene as an olefinic alkylation agent, which further acts as esterification compound during recovery of the acid hydrate.

In the following more detailed description, the invention will further be illustrated by way of examples describing specific embodiments of the invention.

EXAMPLE

In this example trifluoromethanesulphonic acid hydrate with a water content of 13% (w/w) corresponding to a molar ratio water acid of 1.2 : 1 was treated according to a specific embodiment of the invention as described below. The acid hydrate was prepared by evaporation of an aqueous solution of the acid.

In the following experiments, 100 ml acid hydrate 170 g total, 147 g acid +22 g water) were introduced into a 150 ml extraction vessel.

A hydrocarbon feedstream containing 5% 2-butene in isobutane was passed through the vessel at a rate of 5 mi/min. The effluent from the extraction vessel was passed through a 300 ml drying column filled with dry silica (Merck 100, 0.2–0.5 mm) prior to introduction into an alkylation reactor. In the alkylation reactor, the 2-butene was converted to alkylate and the recovered sulphonic acid ester converted to its catalytic active acid form, which was accumulated in the reactor. At the end of each experiment, the amount of acid being in excess of initially loaded acid was removed and water content of the removed acid determined.

In a first experiment, the alkylation reactor was initially loaded with 6 ml (10 g) dry trifluoromethanesulphonic acid (0.28% water). After reaction of 1240 g feed stream (62 g 2-butene) at 25° C., excess of acid was removed from the reactor leaving the same amount of acid in the reactor as at the beginning of the experiment. An excess of 9.4 g of acid with a water content of 0.88% was recovered.

In a second experiment, the alkylation reactor from the first experiment was used without addition of fresh dry acid. The extraction vessel was reloaded with 100 ml acid hydrate and the silica in the drying vessel was replaced.

After 1928 g 5% 2-butene (96.4 g olefin) had passed through the extraction vessel at 40° C, through the drying column and the alkylation reactor, an excess of 8.7 g (94.5% acid, 1.6% water) acid were recovered.

I claim:

1. A process for the alkylation of a hydrocarbon feedstock. With an olefinic alkylating agent by contact with a sulfonic acid catalyst and recovery of a sulfonic acid catalyst from an aqueous extract of an alkylation effluent stream comprising the steps of:

alkylating the hydrocarbon feedstock in an alkylation zone to obtain an alkylation effluent stream;

extracting the alkylation effluent stream with water to obtain an aqueous extract;

evaporating the extract to obtain a hydrate of the sulfonic acid catalyst;

reacting the hydrate with an olefin containing hydrocarbon stream to its corresponding sulfonic acid ester; and introducing the acid ester to the alkylation zone, thereby decomposing the sulfonic acid ester to its catalytically active acid form.

2. The process of claim 1, wherein the sulphonic acid catalyst comprises a halogenated alkyl sulphonic acid.

3. The process of claim 1, wherein the sulphonic acid catalyst comprises a perfluorated alkyl sulphonic acid.

4. The process of claim 1, wherein the sulphonic acid catalyst comprises trifluoromethanesulphonic acid.

5. The process of claim 1, wherein the olefin containing hydrocarbon stream is an alkylation process stream.

6. The process of claim 1, wherein the olefin comprises n-butene.

* * * * *